United States Patent
Murphy

[11] Patent Number: 6,074,421
[45] Date of Patent: Jun. 13, 2000

[54] SEAMLESS BREAST PROSTHESIS

[75] Inventor: Murtagh Murphy, Arklow, Ireland

[73] Assignee: Medisyn Technology, Ltd., Arklow, Ireland

[21] Appl. No.: 09/055,045

[22] Filed: Apr. 3, 1998

[30] Foreign Application Priority Data

Apr. 5, 1997 [EP] European Pat. Off. .............. 97201041

[51] Int. Cl.[7] .................. A61F 2/52; A61F 2/12
[52] U.S. Cl. ..................................... 623/8; 623/7
[58] Field of Search ............. 623/7, 8; 264/222

[56] References Cited

U.S. PATENT DOCUMENTS

| | | | |
|---|---|---|---|
| 3,301,254 | 1/1967 | Schickedanz | 623/7 |
| 5,022,942 | 6/1991 | Yan et al. | 156/219 |
| 5,447,535 | 9/1995 | Muller | 623/8 |
| 5,674,285 | 10/1997 | Quaid | 623/8 |
| 5,895,423 | 4/1999 | Becker et al. | 623/7 |

Primary Examiner—David H. Willse
Assistant Examiner—Suzette J. Jackson
Attorney, Agent, or Firm—Michael G. Petit

[57] ABSTRACT

An improved breast prosthesis or mammary implant (20), is provided of a type known per se, comprising a single or multiple lumen elastic shell or envelope (23), for example of molded silicone, in which an aperture formed in the shell for removal from a mold is subsequently sealed with a silicone patch (24), thus forming internal lumen(s) which can then be filled by either the manufacturer or the surgeon with a fluid or gel. A substantially seamless join between the patch and the shell is formed by means of an aperture with a chamfered edge (22), and applying and bonding a patch to one side, preferably the inside, of the shell such that a seamless and ridgeless join between the patch and the shell is formed to the exterior. A method and apparatus for performing a chamfer trimming operation and applying the patch are also disclosed. A double chamfer aperture edge construction filled in with an overlay patch and an underlay patch is also disclosed.

7 Claims, 3 Drawing Sheets

SEAMLESS BREAST PROSTHESIS

BACKGROUND OF THE INVENTION

The present invention relates to an improved breast prosthesis or mammary implant, of a type known per se, comprising a molded silicone shell or envelope in which an aperture formed in the shell for removal from the mold is subsequently sealed with a silicone patch, thus forming an internal lumen or lumens which can then be filled with a fluid or gel, by either the manufacturer or surgeon. In particular, the present invention relates to a breast prosthesis thus formed with a substantially seamless join between the patch and the lumen.

PRIOR ART

Hitherto, once the shell has been molded on a mandrel, an aperture of about 25 mm in diameter is left for removal of the molded product from the mandrel. On account of the inherent softness and degree of elasticity of the silicone material used, the aperture may be stretched by approximately four hundred per cent to remove the shell from the mandrel. It is generally not possible to make the aperture very much smaller than this if the molded product is to be successfully removed from the mandrel, without overstretching. This aperture has then been sealed by placing an underlay, of greater diameter than the aperture, on one side of the shell, under the aperture, and occasionally, in addition, by placing an overlay, also of greater diameter than the aperture, on the other side of the shell above the aperture, and by bonding these together, in a process used by the applicant. This is essentially a structure which leaves a detectable seam at the transition between the patch material and the shell as well as a ridge on the exterior and interior of the shell at the joins between the underlay/overlay edges and the shell. One of the disadvantages of this construction is that the ridge on the exterior of the finished prosthesis is undesirable from a cosmetic and surgical viewpoint. Also, the process of bonding the overlay onto the shell generally produces a smooth concentric ring around and wider than the smooth central patch area, whereas it would be desirable to maximize the textured surface area of the exterior of the shell right up to the edge of the patch, where this covers or fills in the aperture. Furthermore, the overlapping concentric ring portions of the underlay and the overlay add to the thickness of the shell around the perimeter of the patch where this fills in the aperture, which central portion of the patch is generally the same thickness as the shell. In general, it is desirable to minimize any local thickening of the material.

An alternative structure can be formed using a buttwelded infill plug portion cut to exactly the same dimensions as the aperture opening, strengthened with thinner overlapping overlay and underlay sections, and welded together. However, this does not overcome the problems of an exterior ridge being formed at the joint between the overlay and the shell, and thickening of the prosthesis in a concentric area around the original aperture.

SUMMARY OF THE INVENTION

Accordingly, the present invention provides a breast prosthesis constructed from a single or multiple lumen shell or envelope of elastic material, such as silicone, having an aperture therein for the purpose of removal from a mold, and which aperture is filled in with and sealed by means of a patch construction, thus forming internal lumen(s) which can then be filled by either the manufacturer or the surgeon with a fluid or gel, characterized in that the aperture is formed with a chamfered edge so as to taper out to an internal and/or external surface of the shell, and in that a patch is applied to the said surface and bonded thereto, so as to form a substantially seamless joint on an opposite surface of the shell.

Advantageously, the said surface is defined by the internal surface of the shell, wherein the chamfered edge of the aperture tapers outwardly to the internal surface of the shell.

Alternatively, the said surface is defined by the external surface of the shell, wherein the chamfered edge of the aperture tapers outwardly to the exterior, and furthermore wherein the patch is adapted to be applied to the external surface of the shell. Preferably, in this case, a recess or rebate is formed in the shell surrounding the aperture, for reception of an overlapping portion of the patch, such that a ridgeless join between the patch and the shell is formed at the exterior.

Alternatively, a double chamfer is formed around the aperture edge, tapering out to the internal and the external surfaces of the shell, in which case an overlay patch no larger than the aperture, and an underlay patch larger than the aperture, are used to fill the aperture.

Preferably, the patch is of substantially the same thickness as the shell, of larger size than the aperture. It preferably defines a squared edge, prior to application and bonding to the shell. Alternatively, the patch is of substantially the same size as the aperture, and defines a chamfered edge, corresponding to the chamfer formed on the aperture.

The invention also provides a method of manufacturing a breast prosthesis molded from a single shell or envelope of elastic material, such as silicone, incorporating single or multiple internal lumens which can then be filled with a fluid or gel by either the manufacturer or surgeon, characterized by the steps of;

(a) removing the shell from the mold by means of an aperture formed therein for this purpose;

(b) fitting the molded shell by means of the aperture over a rigid holding member;

(c) advancing a cutting tool towards the shell held on the holding member to trim a portion of the shell surrounding the aperture and form a chamfered edge on the aperture, so as to taper out to an internal and/or external surface of the shell;

(d) removing the shell from the holding member; and (e) applying a patch to the aperture and bonding it to the shell on one side thereof, so as to form a substantially seamless joint on the opposite side thereof Advantageously, the chamfered edge tapers outwardly to the interior surface of the shell, and the patch is applied and bonded from underneath the aperture, underlapping the aperture, so as to form a substantially seamless join with the shell when viewed from the exterior.

DESCRIPTION OF THE PREFERRED EMBODIMENTS

Preferred embodiments of the present invention will now be described with reference to the accompanying drawings, in which:

FIG. 1 is a plan view from above of a textured fluid-filled silicone breast prosthesis sealed by a patch construction in accordance with the prior art;

FIG. 2 is a cross-section, to a slightly enlarged scale, when viewed on section line A—A of the FIG. 1;

FIG. 3 is a plan view from above of a fluid-filled textured silicone breast prosthesis sealed by a seamless patch construction in accordance with the present invention;

FIG. 4 is a cross-section, not exactly to scale, when viewed on section line B—B of FIG. 3;

FIG. 4a shows, in cross-section, an alternative seamless patch construction in accordance with the present invention;

FIG. 4b shows, in cross-section, an alternative seamless patch construction in accordance with the present invention wherein the chamfered edge of the aperture to be sealed by a patch faces outwardly toward the exterior surface of the shell;

FIG. 5 shows trimming apparatus for use in the present invention having a direct cutting action for forming a chamfered edge to a breast prosthesis shell aperture;

FIG. 6 shows a trimming apparatus for use in the present invention having a scissors action for forming a chamfered edge to a breast prosthesis shell aperture;

FIGS. 7 and 7a are cross sections showing another embodiment of the present invention, including a double chamfer arrangement;

FIG. 8 is a cross section showing another embodiment of the present invention, adapted for use in a multiple lumen breast prosthesis, and FIG. 9 is a cross section showing a further embodiment of the present invention, adapted for use in a remote fill multiple lumen breast prosthesis.

BRIEF DESCRIPTION OF THE DRAWINGS

Firstly, referring to FIGS. 1 and 2 of the drawings, which show a prior art method of construction used by the applicant for making a fluid-filled textured silicone breast prosthesis 1, a shell or envelope 2 is formed by a conventional molding process on a mandrel. This is considerably stretched to the maximum limits of the elasticity of the silicone material so as to remove the shell 2 from the mandrel, and is generally about 25 mm (one inch) in diameter. In a conventional process for applying a patch 3 to the aperture, an overlay 4 is applied to the exterior and an underlay 5 is applied to the interior, with respective overlapping portions 6, 7, so as to form a sandwich structure. The overlapping sections of the structure are bonded together, and also those portions of the overlay 4 and underlay 5 which are in contact.

The patch can be bonded to the shell by a variety of means including chemical welding or bonding, ultrasonic welding, and heat/pressure fusing. The disadvantage of this process is that a ridge 8 is formed on the exterior as well as a concentric ring 9 formed by the bonding process, part or all of which may be smooth, i.e. where the textured exterior surface area of the shell 2 may be reduced by the overlap of the overlay 4. This is undesirable, because the exterior textured surface area ought to be maximized for surgical reasons.

FIG. 4 shows a section of shell 23 having an aperture with the chamfered edge 22, tapering outwardly to the interior of the shell. A patch 24 is applied from the interior only and is bonded to the interior surface of the shell and against the chamfered edge by means of an underlapping portion 25 of the patch. However, it should be noted that there is no overlapping portion of the patch on the exterior, and that an essentially seamless joint is formed between the patch and the shell, when viewed from the exterior, as seen in FIG. 3.

Figure 1:
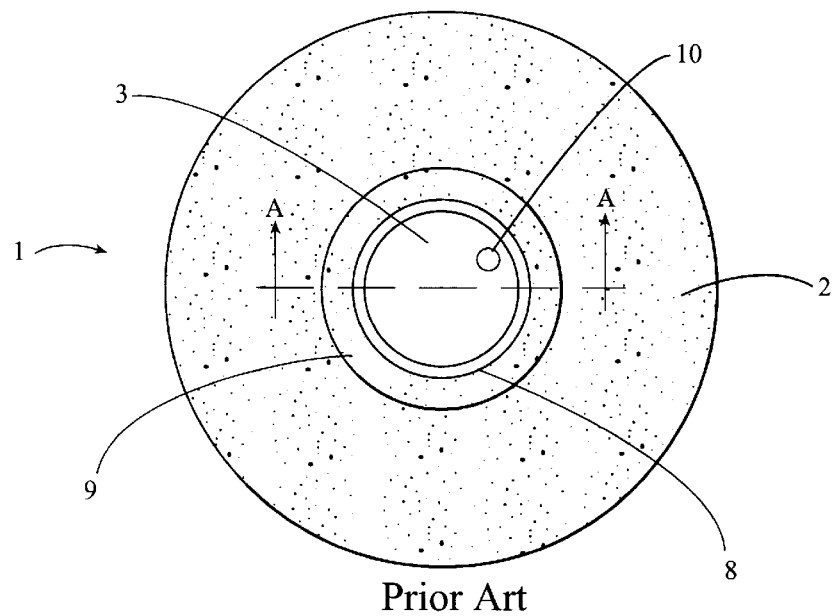
Figure 2:
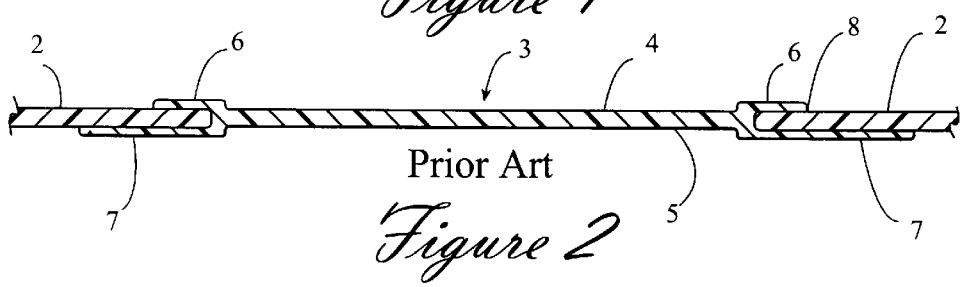
Figure 3:
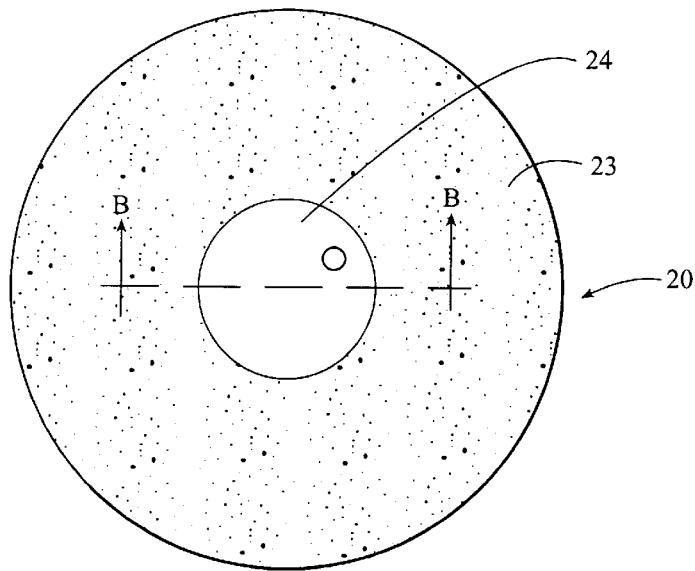
Referring to FIGS. 3 and 4 of the drawings, a fluid-filled textured silicone breast prosthesis 20 in accordance with the present invention is formed from a shell with an aperture on a conventional molding apparatus, and removed therefrom by stretching the aperture over the molding mandrel. At this stage, the edge of the aperture is squared, i.e. of the conventional type. This is then stretched over an insert or holding member 30 of a trimming apparatus, as shown in FIG. 5. The squared edge 21 of the shell aperture can be seen in FIG. 5. A chamfered edge 22 (see FIG. 4) is formed on the shell aperture by a blade 31 mounted on a piston and cooperating with the insert 30, which defines an inclined surface 32 against which the blade 31 makes contact so as to trim off a small ring of waste material and leave a chamfered edge 22 around the aperture. If necessary, the shell may be inverted or turned inside out when performing the trimming step.
Figure 4:
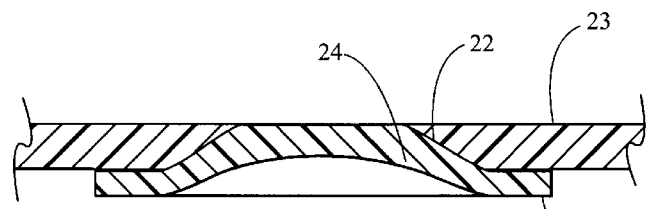
Figure 4A:
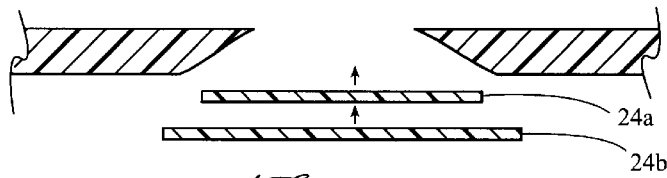

Alternatively, as shown in FIG. 4a, the patch applied from the interior may comprise two parts, a cap plug portion 24a, slightly larger than the aperture, and an underlay portion 24b, larger still, such that when bonded together, the whole patch underlaps the aperture in the same manner illustrated in FIG. 4.

The configurations shown in FIGS. 4 and 4a have the advantage that a better stronger bond is formed between the edge of the aperture and the patch, since the edge area is increased by virtue of the chamfer, when compared to a squared edge, and that no ridge is formed on the exterior at the joint between the patch and the shell. It will be appreciated that the presence of any detectable seam between the patch and the shell represents a stress point which could possibly fail giving rise to leakage of fluid from the prosthesis, which must be avoided. Furthermore, the bonding process may be performed such that the textured surface area of the shell surrounding the aperture to the exterior is not compromised, i.e. by smoothening out a ring around the patch as in the prior art, thereby maximizing the textured surface area on the exterior of the prosthesis.

There are final curing, vulcanizing, filling, sterilizing and closing steps which are essentially the same as in the prior art and need not be described in detail, in order to provide the finished prosthesis. The filling of the internal lumen(s) can be done by either the manufacturer or the surgeon. In general, prostheses which are to be gel-, oil-, or foam-filled are pre-filled by the manufacturer, and prostheses which are to be filled with saline have the saline added by the surgeon.

Figure 4B:
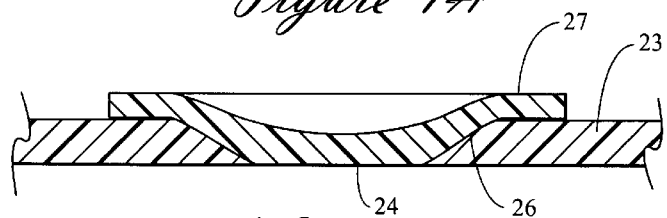
Figure 5:
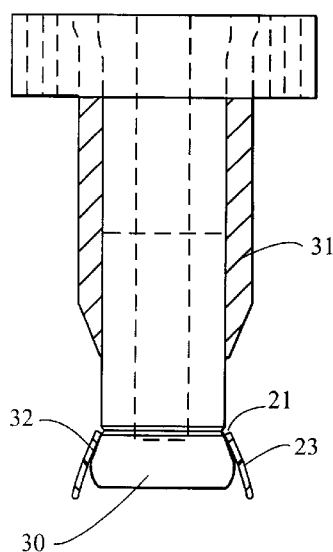

FIG. 4b shows an alternative patch construction in accordance with the present invention, in which a chamfered edge 26 is formed in the shell 23, tapering outwardly to the exterior of the shell. However, in order to apply a patch to the aperture with a completely ridgeless join to the exterior, it may be necessary to form an additional recess or rebate 27 into which the patch must be fitted precisely to fill the recess, prior to bonding. However, this is a more difficult process and requires much finer tolerances, whereas in the embodiment shown in FIG. 4, the degree of the underlap 25 is not significant and any ridge formed to the interior after bonding of the patch to the shell is also not of great significance.

Figure 6:
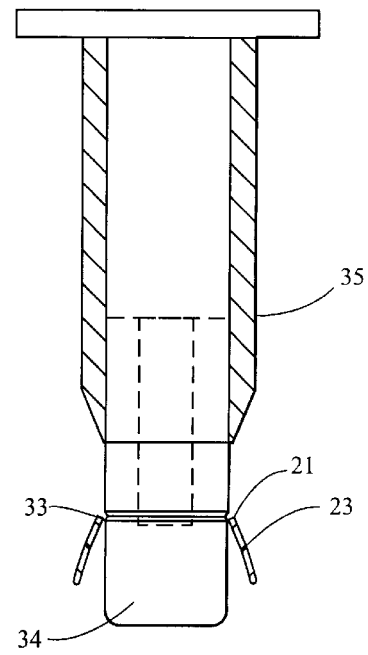

FIG. 6 shows an alternative trimming apparatus which operates by means of a scissors action. The squared edge 21 of the aperture is stretched over an inclined groove 33 formed in a cylindrical holding member or insert 34, such that the cutting blade 35 slides over the insert 34 to snip off a waste ring of material and cause a chamfered edge to be formed around the aperture. The chamfered edge has to be cut with care on account of the high degree of elasticity and softness of the silicone material, and the desirability of forming a clean cut chamfered edge.

Other methods and apparatus are possible for precisely forming a clean chamfer on the edge of the shell aperture, such as laser or ultrasonic cutting, as opposed to the mechanical method described above which utilizes a blade. With modification of the shell material, direct forming of the chamfer in one step during molding, by injection-, rotary-, or blow-molding techniques should be possible. Such other methods of forming the chamfer will become apparent to those skilled in the art, and do not lie outside the scope of the present invention.

Figure 7:
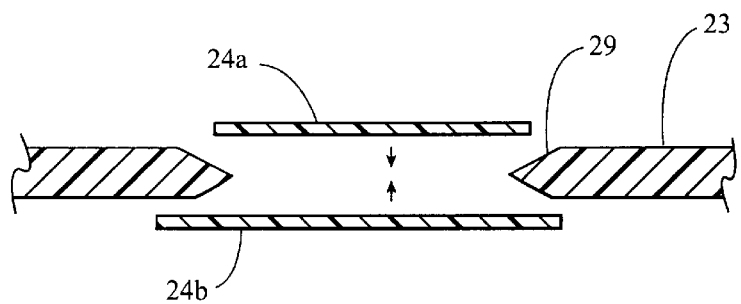
Figure 7A:
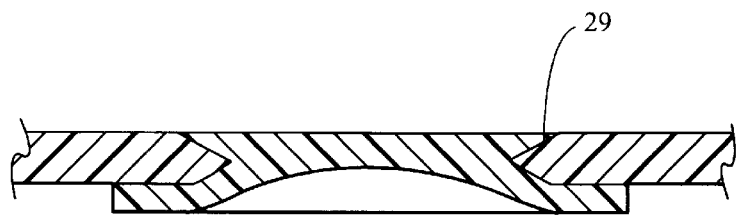

FIG. 7 shows another embodiment of the invention, where the aperture in the shell 23 is formed with a double chamfered edge 29. A two-part patch comprising an overlay plug portion 24*a*, applied from the exterior, and a thin underlay portion 24*b*, applied from the interior, are used to fill the aperture, such that when bonded together, a substantially seamless patch is provided, as viewed from the exterior (see FIG. 7*a*).

Figure 8:
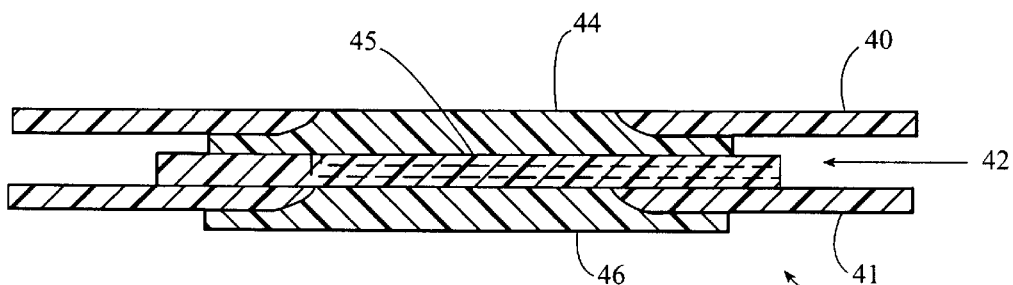
Figure 9:
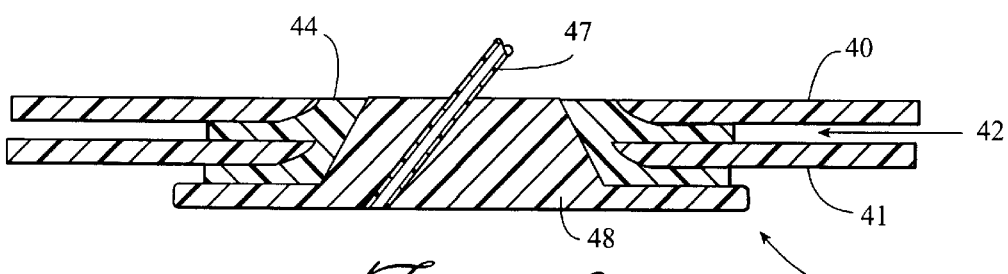

FIGS. 8 and 9 show further embodiments of the invention, providing a substantially seamless patch construction for breast prostheses having multiple internal lumens. FIG. 8 shows a multiple lumen device having an outer shell 40, an inner shell 41, an outer lumen 42 which may for example be filled with saline, an inner lumen 43 which may for example be filled with a gel, an outer patch 44, an intermediate plug portion 45 incorporating a valve and valve channel (dashed outline), and an inner patch 46. FIG. 9 shows a multiple lumen device having an outer shell 40, an inner shell 41, an outer lumen 42 which may for example be filled with gel, an inner lumen 43 which may for example be filled with saline through a filling port 47, a patch 44 comprising outer and inner patches formed as rings and bonded together as shown, and a molded component 48 with a raised chamfered central portion. In both cases, it will be seen that the patches 44, 46, are applied from the inside of the respective shell 40, 41, against a chamfered edge formed on the shell apertures.

What I claim is:

1. A breast prosthesis comprising a shell of elastic material having an outer surface, an inner surface and an aperture therein for the purpose of removing the shell from a mold, and which aperture is sealed by means of a patch thereby forming internal lumen which can be filled with a fluid or gel, wherein said aperture has a chamfered edge.

2. A breast prosthesis according to claim 1 wherein the chamfered edge of the aperture tapers outwardly toward said outer surface of the shell.

3. A breast prosthesis according to claim 1 wherein the chamfered edge of the aperture tapers outwardly toward said inner surface of the shell.

4. A breast prosthesis according to claim 3, wherein a annular recess is formed in the shell surrounding the aperture, for reception of an overlapping portion of the patch, such that a ridgeless joint is formed between the patch and said outer surface of the shell.

5. A breast prosthesis according to claim 1, in which a double chamfer is formed around the aperture edge, tapering outwardly toward said outer surface and said inner surface of said shell and wherein an overlay patch no larger than the aperture and an underlay patch larger than the aperture fill the aperture.

6. A breast prosthesis according to claim 1 wherein said shell has a thickness and wherein the patch is of substantially the same thickness as the shell and has a larger diameter than the aperture.

7. A breast prosthesis according to claim 1, in which the patch is of substantially the same size as the aperture and has a chamfered edge matingly corresponding to the chamfer formed on the aperture.

* * * * *